(12) United States Patent
DaQuino et al.

(10) Patent No.: US 7,005,293 B2
(45) Date of Patent: Feb. 28, 2006

(54) MULTIPLE AXIS PRINTHEAD ADJUSTER FOR NON-CONTACT FLUID DEPOSITION DEVICES

(75) Inventors: Lawrence J. DaQuino, Los Gatos, CA (US); Richard P. Tella, Sunnyvale, CA (US)

(73) Assignee: Agilent Technologies, Inc., Palo Alto, CA (US)

(*) Notice: Subject to any disclaimer, the term of this patent is extended or adjusted under 35 U.S.C. 154(b) by 438 days.

(21) Appl. No.: 10/022,065

(22) Filed: Dec. 18, 2001

(65) Prior Publication Data

US 2003/0113729 A1 Jun. 19, 2003

(51) Int. Cl.
*C12M 1/34* (2006.01)
*C12Q 1/68* (2006.01)
*C12P 19/34* (2006.01)
*C07H 21/02* (2006.01)
*C07H 21/04* (2006.01)

(52) U.S. Cl. ............... 435/287.2; 435/6; 435/7.1; 435/91.1; 435/91.2; 435/285.1; 536/22.1; 536/23.1; 536/24.3; 536/24.31; 536/24.32; 536/24.33; 536/24.34; 358/1.1; 347/19

(58) Field of Classification Search ............ 435/6, 435/7.1, 91.1, 91.2, 285.1, 287.2; 536/221, 536/231, 24.3–24.33; 358/1.1; 347/19
See application file for complete search history.

(56) References Cited

U.S. PATENT DOCUMENTS

| 4,500,895 A | 2/1985 | Buck et al. |
| 4,771,295 A | 9/1988 | Baker et al. |

(Continued)

FOREIGN PATENT DOCUMENTS

| EP | 0 824 074 | 2/1998 |
| EP | 0 938 973 | 9/1999 |
| EP | 1 093 855 | 4/2001 |
| WO | WO 98/41631 | 9/1998 |

OTHER PUBLICATIONS

Roda, A. et al., "Protein Microdeposition Using a Conventional Ink–Jet Printer", Bio Techniques, vol. 28, No. 3 (2000), pp. 492–496.

Communication from the European Patent Office dated Mar. 11, 2004, enclosing the European Seach Report for EP Appln. No. 02 26 8742, counterpart of US Appln. No. 10/022,065.

*Primary Examiner*—Jeffrey Siew (57) ABSTRACT

Non-contact fluid deposition devices having multiple axis printhead adjusters are provided. The subject printhead adjusters are made up of a single rigid frame that holds at least one printhead housing, where in certain embodiments multiple printhead housings, e.g., two, are held in side-by-side configuration in the single rigid frame of the adjuster. Each housing is adjusted in said adjuster by its own set of axis adjustment elements, where the set includes a rotational axis adjustment element for each horizontal and/or vertical axis adjustment element that is present. In using the subject devices, a printhead present in the adjuster is loaded with a volume of fluid, which in many embodiments is a fluid that includes a biopolymer or precursor thereof. The loaded printhead is then placed in opposing relation to a surface of a substrate and actuated to deposit a volume of fluid on the substrate. Prior to fluid loading and/or deposition, the printhead is typically adjusted with the set of axis adjustment elements. The subject invention finds use in a variety of applications, including the production of biopolymeric arrays.

62 Claims, 6 Drawing Sheets

U.S. PATENT DOCUMENTS

| | | | |
|---|---|---|---|
| 4,877,745 | A | 10/1989 | Hayes et al. |
| 5,278,584 | A | 1/1994 | Keefe et al. |
| 5,305,015 | A | 4/1994 | Schantz et al. |
| 5,449,754 | A | 9/1995 | Nishioka |
| 5,474,796 | A | 12/1995 | Brennan |
| 5,658,802 | A | 8/1997 | Hayes et al. |
| 5,700,637 | A | 12/1997 | Southern |
| 5,755,520 | A * | 5/1998 | Furlani et al. .............. 400/354 |
| 5,958,342 | A | 9/1999 | Gamble et al. |
| 6,155,675 | A | 12/2000 | Nice et al. |
| 6,155,676 | A | 12/2000 | Etheridge et al. |
| 6,183,067 | B1 | 2/2001 | Matta |
| 6,221,653 | B1 | 4/2001 | Caren et al. |
| 6,242,266 | B1 | 6/2001 | Schleifer et al. |
| 6,248,521 | B1 | 6/2001 | Van Ness et al. |
| 6,290,331 | B1 | 9/2001 | Agarwal et al. |
| 6,568,786 | B1 * | 5/2003 | Sarmast et al. ............... 347/19 |

* cited by examiner

MULTIPLE AXIS PRINTHEAD ADJUSTER FOR NON-CONTACT FLUID DEPOSITION DEVICES

INTRODUCTION

1. Field of the Invention

The field of this invention is biopolymeric microarrays, and particularly devices for producing such arrays.

2. Background of the Invention

Arrays of biopolymeric binding agents, such as oligonucleotides and peptides, have become an increasingly important tool in the biotechnology industry and related fields. These binding agent arrays, in which a plurality of binding agents are present on a solid support surface in the form of an array or pattern, find use in a variety of applications, including genomomics and proteomics applications, e.g., gene expression analysis, drug screening, nucleic acid sequencing, mutation analysis, proteome analysis, and the like.

Such arrays may be prepared in a number of different ways. For example, DNA arrays may be prepared manually by spotting DNA onto the surface of a substrate with a micro pipette. See Khrapko et al., DNA Sequence (1991) 1:375–388. Alternatively, the dot-blot approach, as well as the derivative slot-blot approach, may be employed in which a vacuum manifold transfers aqueous DNA samples from a plurality of wells to a substrate surface. In yet another method of producing arrays of biopolymeric molecules, a pin is dipped into a fluid sample of the biopolymeric compound and then contacted with the substrate surface. By using a plurality or array of pins, one can transfer a plurality of samples to the substrate surface at the same time. Alternatively, an array of capillaries can be used to produce biopolymeric arrays. See WO 95/35505. In another method of producing biopolymeric arrays, arrays of biopolymeric agents are "grown" on the surface of a substrate in discreet regions. See e.g. U.S. Pat. No. 5,143,854 and Fodor et al., Science (1991) 251:767–773.

One type of biopolymeric array fabrication process of particular interest is the jet printing fabrication protocol, in which thermal or piezo pulse jet devices analogous to inkjet printing devices are employed to deposit fluids of biopolymers or precursors therefore onto a substrate surface. For example, Roda et al., Biotechniques (2000) 28:492–496, describe a method in which a conventional inkjet printer is used for the microdeposition of proteins. In this report, the black ink was removed from a Hewlett Packard ink cartridge and the cartridge was extensively washed with water. The cartridge was filled with the protein deposition solution using a microsyringe and sealed. Similarly, Deeg et al. in U.S. Pat. No. 5,338,688, describe a method of using bubble-jet technology for the metered application of an analytical liquid to a target. This disclosed method is based on the manufacture of disposable jet units containing the analytical liquid in prepacked form. Additional U.S. patents disclosing thermal and/or piezo pulse jet deposition of biopolymer containing fluids onto a substrate include: U.S. Pat. Nos. 4,877,745; 5,449,754; 5,474,796; 5,658,802; 5,700,637; and 5,958,342.

Despite the advances made to date in the arena of pulse jet printing of biopolymeric arrays, there is a continued need for improvement in this field. Of particular interest would be the development of highly accurate pulse jet printing devices that are able to print a multitude of different fluids at the same time, where the devices require little maintenance and yet produce high quality, dense arrays.

3. Relevant Literature

U.S. Pat. Nos. 4,877,745; 5,449,754; 5,474,796; 5,658,802; 5,700,637; and 5,958,342; 6,221,653; and 6,242,266. Additional U.S. patents of interest that describe traditional thermal inkjet devices and methods for their use in ink deposition include: U.S. Pat. Nos. 4,500,895; 4,771,295; 5,278,584; 5,305,015; 6,155,675; 6,155,676; 6,183,067; 6,290,331; See also: The Hewlett-Packard Journal, Vol. 39, No. 4 (August 1988).

SUMMARY OF THE INVENTION

Non-contact fluid deposition devices having multiple axis printhead adjusters are provided. The subject printhead adjusters are made up of a single rigid frame that holds at least one printhead housing, where in certain embodiments multiple printhead housings, e.g., two, are held in side-by-side configuration in the single rigid frame of the adjuster. Each housing is adjusted in the frame by its own set of axis adjustment elements, where the set includes a rotational axis adjustment element for each horizontal and/or vertical axis adjustment element that is present. In using the subject devices, a printhead present in the adjuster is loaded with a volume of fluid, which in many embodiments is a fluid that includes a biopolymer or precursor thereof. The loaded printhead is then placed in opposing relation to a surface of a substrate and actuated to deposit a volume of fluid on the substrate. Prior to fluid loading and/or deposition, the printhead is typically adjusted with the set of axis adjustment elements. The subject invention finds use in a variety of applications, including the production of biopolymeric arrays.

DEFINITIONS

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to up to about 100 nucleotides in length.

The term "polynucleotide" as used herein refers to a single or double stranded polymer composed of nucleotide monomers of generally greater than 100 nucleotides in length and up to about 8,000 or more nucleotides in length. Polynucleotides include single or multiple stranded configurations, where one or more of the strands may or may not be completely aligned with another.

A "nucleotide" refers to a subunit of a nucleic acid and includes a phosphate group, a 5 carbon sugar and a nitrogen containing base, as well as analogs of such subunits.

The term "peptide" as used herein refers to any compound produced by amide formation between a carboxyl group of one amino acid and an amino group of another group.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "array" as used herein means an substrate having a plurality of binding agents stably attached to its surface, where the binding agents may be spatially located across the surface of the substrate in any of a number of different patterns.

The term "binding agent" means any agent that is a member of a specific binding pair, where such agents include: peptides, e.g. proteins or fragments thereof; nucleic acids, e.g. oligonucleotides, polynucleotides; and the like; etc.

The term "biopolymer" includes peptides or polynucleotides, as well as such compounds composed of or containing amino acid or nucleotide analogs or non-nucleotide groups. As such, this term includes those compounds in which the conventional polynucleotide backbone has been replaced with a non-naturally occurring or synthetic backbone, and those a nucleic acid in which one or more of the conventional bases has been replaced with a synthetic base capable of participating in Watson-Crick type hydrogen bonding interactions.

A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a fluid containing either a biomonomer or biopolymer, respectively.

Reference to a "droplet" being dispensed from a pulse jet herein, merely refers to a discrete small quantity of fluid (usually less than about 1000 pL) being dispensed upon a single pulse of the pulse jet (corresponding to a single activation of an ejector) and does not require any particular shape of this discrete quantity.

"Fluid" is used herein to reference a liquid. Further, when reference is made in this application to providing a pressure within the dispensing head or a chamber therein this refers, unless a contrary indication appears, to a pressure therein relative to the pressure immediately outside the head pulse jet orifices. Such pressures can be provided by varying the pressure outside the head, or inside the head, or both.

The term "printhead" refers to an integrated structure that includes an orifice plate and at least one printhead dye affixed thereto.

The term "printhead assembly" refers to a printhead affixed to a structural element, where the structural element may or may not include one or more fluid reservoirs.

The term "printhead housing" refers to a housing structure that holds a printhead assembly.

The term "printhead adjuster" refers to a composite structure that includes a printhhead housing held in a frame.

DESCRIPTION OF THE SPECIFIC EMBODIMENTS

Non-contact fluid deposition devices having multiple axis printhead adjusters are provided. The subject printhead adjusters are made up of a single rigid frame that holds at least one printhead housing, where in certain embodiments multiple printhead housings, e.g., two, are held in side-by-side configuration in the single rigid frame of the adjuster. Each housing is adjusted in the frame by a set of axis adjustment elements, where the set includes a rotational axis adjustment element for each horizontal and/or vertical axis adjustment element that is present in the frame. In using the subject devices, a printhead present in the adjuster is loaded with a volume of fluid, which in many embodiments is a fluid that includes a biopolymer or precursor thereof. The loaded printhead is then placed in opposing relation to a surface of a substrate and actuated to deposit a volume of fluid on the substrate. Prior to fluid loading and/or deposition, the printhead is typically adjusted with the set of axis adjustment elements. The subject invention finds use in a variety of applications, including the production of biopolymeric arrays.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the invention components which are described in the publications which might be used in connection with the presently described invention.

As summarized above, the subject invention provides non-contact fluid deposition devices that include a printhead adjuster having a set of multiple axis adjustment elements, as well methods of using the subject devices in fluid deposition applications, e.g., in the deposition of biopolymer/biomonomer fluids onto a substrate, e.g., for the production of biopolymeric arrays. In further describing the subject invention, the subject printhead devices and components thereof are described first in greater detail, followed by a review of methods for using the same as well as other aspects of the invention.

Non-contact Fluid Deposition Devices

As summarized above, the subject invention provides non-contact fluid deposition device for depositing fluid onto the surface of a substrate. The subject devices are characterized in that they include a printhead adjuster that includes a single rigid frame holding at least one printhead housing. A feature of the printhead adjusters of the subject invention is that each of the one or more printhead housings is adjusted in, i.e., moved relative to, the single rigid frame with a set of axis adjustment elements, which set includes a rotational axis adjustment element for each horizontal and/or vertical axis adjustment element in the set, e.g., rotational theta about X for X; rotational theta about Y for Y and rotational theta about Z for Z. Typically, each set includes at least one horizontal adjustment clement and a vertical adjustment element, where the set further includes a rotational axis adjustment element for each horizontal and vertical axis adjustment element of the set. Often, each set includes two horizontal axis adjustment elements, e.g., an X and Y axis adjustment element; and one vertical axis adjustment element, e.g., a Z axis adjustment element. By axis adjustment element is meant a single component, e.g., a screw component as discussed in greater detail below, or two or more components, e.g., multiple screw elements, that work in combination to move or adjust position in a given axis, e.g., move in the same direction to adjust position.

As the subject printhead adjusters of the present invention include at least one printhead housing, in many embodiments the subject printhead adjusters include multiple printhead housings. By "multiple printhead housings" is meant a plurality of two or more printhead housings. The total number of printhead housings in many embodiments ranges from 2 to about 10, typically from 2 to about 5 and often from 2 to about 3. When multiple printhead housings are present in the subject printhead adjusters, they are typically configured in a side-by-side manner.

The single rigid frame component of the subject adjusters is typically square or rectangular in shape. While the dimensions of the frame may vary significantly, e.g., depending on the number of housings held therein, in many embodiments the frame component has a length ranging from about 30 to about 500 mm, usually from about 50 to about 300 mm and more usually from about 75 to about 200 mm.

As mentioned above, a feature of the subject adjusters is that each printhead housing is adjusted in the frame component of the adjuster by a set of axis adjustment elements. In other words, a plurality of or multiple axis adjustment elements adjust each housing element in the frame of the adjuster, where the plurality of individual axis adjustment elements is collectively referred to as a set. When the adjuster includes more than one printhead housing, each housing is adjusted in the frame by its own set of axis adjustment elements. Where multiple printhead housings are present in a given adjuster, and therefore multiple sets of individual axis adjustment elements are present, there is typically an identical number individual axis adjustment elements in each set. For example, where a representative given adjuster includes two different housings, such as the one depicted in FIGS. 3 and 4 of this application and discussed in greater detail below, each housing is adjusted in the frame by its own set of six different individual axis adjustment elements, and the total number of individual axis adjustment elements in the adjuster is twelve.

Figure 1:
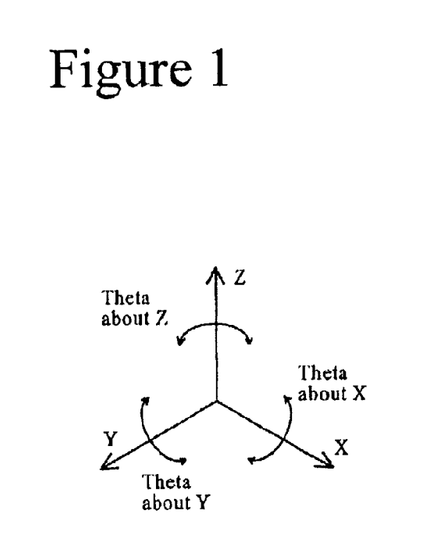
FIG. 1 provides an illustration of the different directions in which a representative six-way adjuster moves a printhead housing present in the adjuster.

An important feature of the subject invention is that any given set of individual axis adjustment elements, i.e., collection or plurality of individual axis adjustment elements, includes a rotational axis adjustment element for each horizontal and/or vertical axis adjustment element that is present in the set. For example, where the set includes three horizontal/vertical axis adjustment elements, it also includes a rotational axis adjustment element for each of these three different axis adjustment elements. As such, in this representative embodiment the set includes six different individual axis adjustment elements. In many embodiments, each housing is adjusted in the single rigid frame with six different individual axis adjustment elements, made up of three vertical/horizontal axis adjustment elements and three corresponding rotational axis adjustment elements, where in many embodiments, the six individual axis adjustment elements are: X axis adjustment element; theta about X axis adjustment element; Y axis adjustment element; theta about Y axis adjustment element; Z axis adjustment element; and theta about Z axis adjustment element. See e.g., FIG. 1, which provides an illustration of the different directions for each axis adjustment element in these sets.

The individual adjustment elements are typically fine pitch screws that thread through a receiving bolt and/or drilled hole through the frame wall and contact a side of the printhead housing held inside the frame. The fine pitch screw of the adjustment element has a pitch that typically ranges from about 56 to about 120, usually from about 80 to about 100 threads/inch. The ball end of the fine pitch screw is threaded through appropriate opening in the frame wall and sits on a hard pad element present on the housing. The hard pad element on the housing typically has sufficient hardness such that it will not dimple, typically having a hardness as registered on the Mohs scale of at least about 9, usually at least about 7 and more usually at least about 5. The hard pad is typically coated with a high contact force lubrication element, e.g., extreme pressure lube; center point lube; and the like; which provides for reduced friction.

Figure 2A:
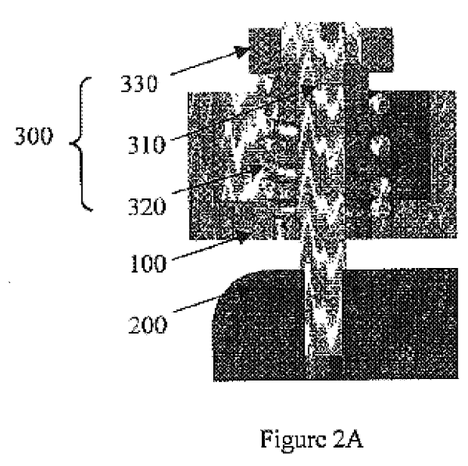
FIGS. 2a and 2b provide a cut-away views of a representative spring/screw holding element that finds use in the subject printhead adjusters.
Figure 2B:
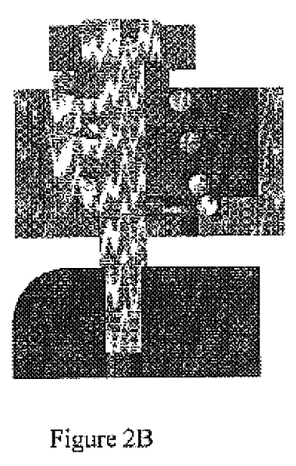

Each of the housings in the printheads is held in the frames by one or more frictionless holding elements. These one or more holding elements hold each printhead housing in the frame in manner that provides for little if any movement of the printhead housing relative to the frame during use, e.g., during fluid deposition, and yet are substantially frictionless elements. The number of different holding elements per housing in the frame may vary, but typically ranges from about 3 to about 21, usually from about 5 to about 12. In many embodiments, each holding element includes a spring and screw that, in combination, hold the housing in the frame and allow adjustment of the housing by the adjustment elements relative to the frame without any sliding friction from the spring component of the holding element. FIGS. 2a and 2b provide cutaway views of a representative individual spring/screw holding elements that find use in the subject printhead adjusters. In FIG. 2a, frame component 100 and housing 200 are held relative to each other by individual holding element 300 that is made up of screw 310 passing through spring 320, where the spring and screw are held in place relative to each other between shoulder washer 330 and frame, specifically a depressed chamber in the frame which has dimensions sufficient to hold the spring and screw, i.e., has a diameter that is larger than the outer diameter of the spring, e.g., by at least about 5, and sometimes by at least about 10 mm, where the depth of this chamber typically ranges from about 1 to about 20, usually from about 5 to about 10 mm. It is important to note that the large depressed chamber is not critical to the functionality of the adjuster. In certain embodiments, the large depressed chamber is present because the springs and screws will interfere with the vision system. Recessing the springs and screws into the thick frame gets them out of the way of the lens and makes the assembly look cleaner. As such, included within the scope of the invention are embodiments that do not include a large, depressed chamber. To provide for the low friction holding system of the subject invention, the outer diameter of screw 310 is less than the inner diameter of spring 320. The magnitude of the difference typically ranges from about 2 to about 8 mm, usually from about 3 to about 5 mm. While the dimensions of screw 310 will necessarily vary, in many embodiments the screws have an end-to-end length of from about 6 to about 50 mm, usually from about 10 to about 25 mm. The spring component of the subject holding elements is one that provides for a force that is low enough to avoid stiction at the fine pitch screw/hard pad interface of the adjustment element described above, but is sufficiently great to provide for no mobility of the printhead relative to the frame during use, e.g., during printing and washing. In many embodiments, the force of the spring that is present in the axis holding element ranges from about 0.2 to about 20 lb, usually from about 0.5 to about 10 lb, where the spring is typically made up of a wire having a diameter ranging from about 0.3 to about 3 mm, usually from about 0.5 to about 1.5 mm. The screws of the holding elements screw into mating holes 210 present in the printhead housing 200, thereby holding the printhead housing in the frame. The individual components of the subject axis holding elements described above (as well as any other components of the printhead adjusters and devices comprising the same as described herein) may be made up of any convenient materials, where representative materials include metals, e.g., aluminum, brass, carbon steel, stainless steel; plastics such as delrin, polycarbonate, acrylic;and the like.

The printhead housing component of the subject printhead adjusters is a housing structure designed to hold/secure a printhead or assembly thereof, such that the printhead is held by the printhead adjuster which in turn is held by a translational arm of a fluid deposition device according to the subject invention. The housing is therefore configured to engagingly fit with or connect to a printhead or assembly thereof. In principle, the housing is configured to fit with any type of printhead assembly, including pulse jet assemblies, such as piezoelectric and thermal pulse jet assemblies. In many embodiments, the printhead housing is configured to engagingly secure or hold a multiple printhead die/multiple reservoir printhead assembly as described in copending U.S. application Ser. No. 10/022,088 the disclosure of which is herein incorporated by reference.

The overall dimensions of the printhead housing may vary, particularly with respect to the nature of the printhead and assembly thereof that is designed to hold. However, in many embodiments, the printhead housing is configured to have a length ranging from about 20 to about 200 mm, usually from about 40 to about 100 mm, a height ranging from about 20 to about 100 mm, usually from about 30 to about 80 mm and a width ranging from about 20 to about 100 mm.

A feature of the subject printhead housings in many embodiments, e.g., those embodiments where the axis adjustment elements are fine pitch screw adjustment elements as described above, is that the printhead housing has a hard pad for each adjustment element. For example, where the printhead adjuster includes six individual axis adjuster elements for each printhead housing in the rigid frame, the printhead housing has six different hard pads, one for each adjuster element. The six different hard pads are positioned on the sides and top of the printhead housing in locations sufficient to provide for the desired vertical, horizontal and rotational movement of the printhead housing in the rigid frame.

In addition, the printhead housing includes one or more receiving holes for the screws of the frictionless holding elements, as described above. The holes are typically positioned on the sides and top of the housing, and typically number from about 3 to about 10, usually from about 5 to about 7. They are dimensioned to provide for engagement with the screw component of the holding element, and therefore typically have a diameter ranging from about 2 to about 5 mm, usually from about 2.5 to about 4 mm and a depth ranging from about 2 to about 20 mm, usually from about 3 to about 10 mm.

The printhead housings typically include the following additional components. First, the printhead housings typically include printhead assembly alignment elements for accurately positioning a printhead assembly inside the printhead housing. The alignment element present in a given printhead housing may take a number of different configurations, but typically includes two or more dowels or analogous alignment means that mate with structures on the printhead assembly to accurately position the printhead assembly in the housing. Another element typically present in the subject printhead housings is a compression means for establishing a fluid seal between an external fluid line and a printhead assembly present in the housing. Any convenient compression means may be present for this purpose, where in many embodiments the compression means is an engaging screw. Yet another element that is typically present in the subject printhead housings is a compression means for electrically engaging an electrical connector board held in the housing with the printhead assembly held in the housing. In many embodiments, this compression means is a thumb screw, but other compression means are also possible.

Figure 3:
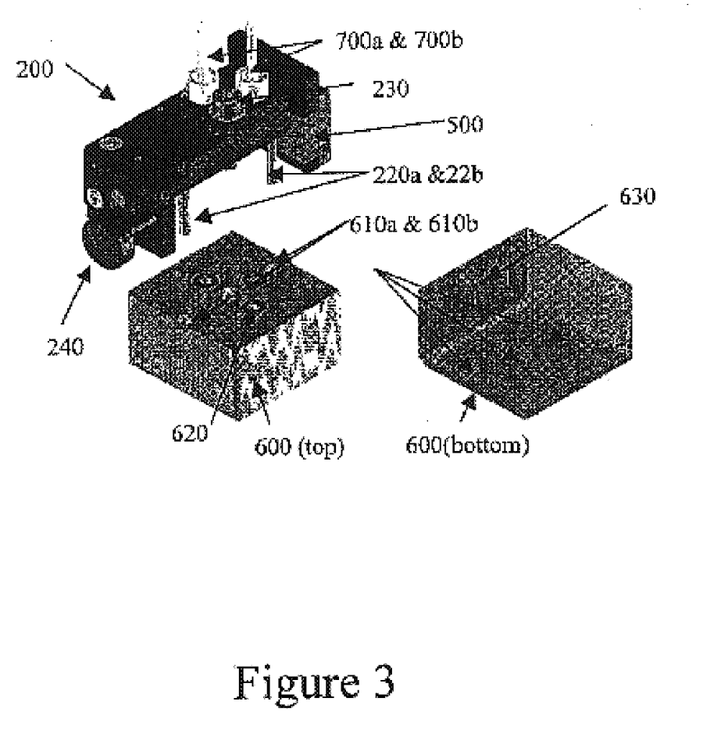
FIG. 3 provides a cut-away view of a representative printhead housing found in an adjuster according to the subject invention.

A cutaway view of a representative printhead housing is provided in FIG. 3. In FIG. 3, housing 200 slides over printhead assembly 600 to engagingly hold the printhead assembly 600 in the printhead housing. The printhead housing includes two dowel pins 220*a* and 220*b* that fit into corresponding holes 610*a* and 610*b* in the printhead assembly. Also shown are fluid lines 700*a* and 700*b* on the top of the printhead assembly. The fluid lines are sealing engaged with the printhead assembly in the housing by engaging screw 230 that securingly holds the printhead assembly in the housing and presses the housing and fluid lines onto the O-rings 620 on the surface of the printhead assembly, thereby making a fluid seal. In addition, thumbscrew 240 is turned to engage the electrical connections of the electrical connector board 500 with the electrical pads 630 of the printhead assembly.

Figure 4:
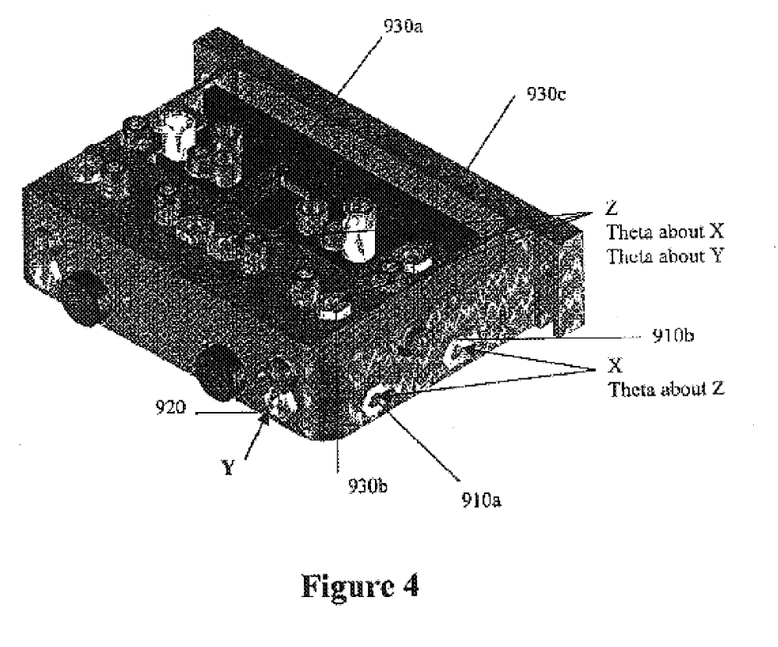
FIG. 4 provides a three dimensional view of a representative 12 axis printhead adjuster that includes two different printhead housings in a single rigid frame.
Figure 5:
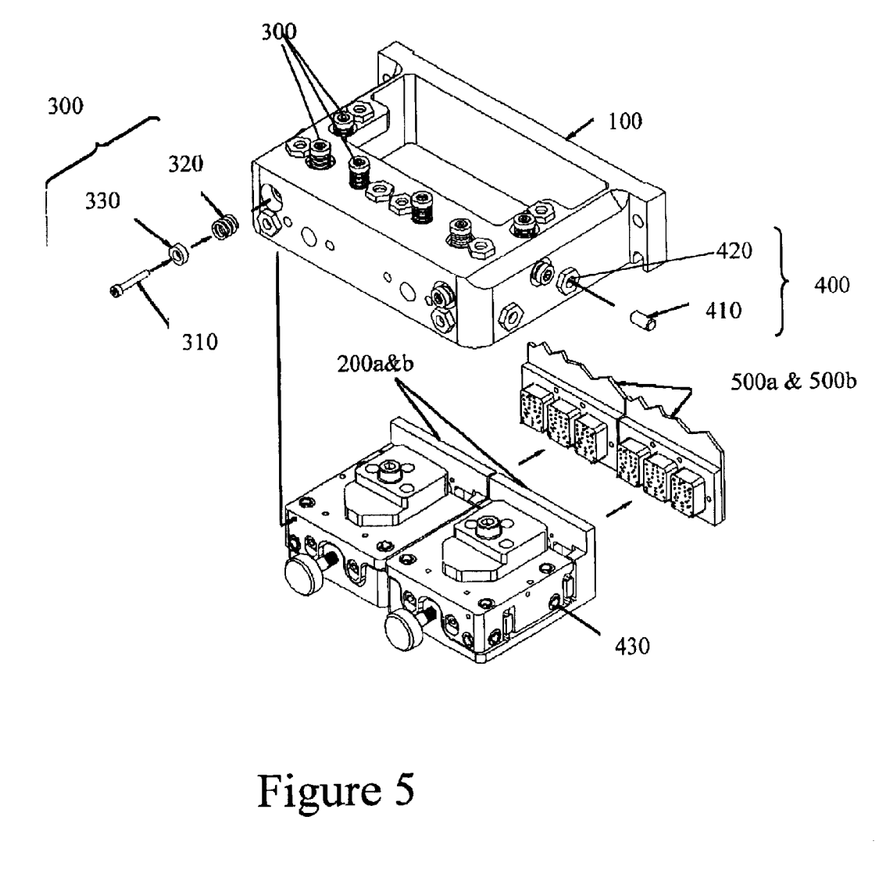
FIG. 5 provides an exploded view of the representative printhead adjuster shown in FIG. 3.

The subject printhead adjusters having been generally described above, further description of the subject adjusters is now provided in terms of a representative two printhead housing adjuster depicted in the figures. FIG. 4 provides a three dimensional view of a representative 12 axis printhead adjuster that includes two different printhead housings in a single rigid frame. FIG. 5 provides an exploded view of the representative printhead adjuster shown in FIG. 4. In FIG. 5, single rigid frame 100 is a rectangular structure that holds two printhead housings 200a & 200b in a side-by-side configuration in the frame. The two different printhead housings are held in the frame by multiple screw/spring holding elements 300, each made up of made up of screw 310, spring 320 and should washer 330. Also shown in FIGS. 4 and 5 are multiple adjustment elements 400 each made up of a fine pitch screw 410 that thread through bolt 420 in frame 100 so that the ball end of the screw 410 contacts hard pad 430 on the side of the printhead housing. The three adjustment elements on top of the adjuster are for adjustment in Z axis, and theta about X and Y axes. The two adjuster elements shown on the one side of the frame are for adjustment in the X axis and theta about Z axis. The single adjustment element shown on the adjacent side of the frame is for adjustment in the Y axis. Also shown in FIG. 5 are electrical connector boards 500a and 500b for connecting with printhead assemblies held by the printhead housings of the adjuster.

The above described printhead adjusters find use with a variety of different non-contact fluid printhead assemblies and printing devices. In many embodiments, the above described printhead adjusters are employed with pulse jet printhead assemblies, e.g., piezoelectric and thermal pulse jet printhead assemblies. Such assemblies are well known in the fluid deposition art, and are described in: U.S. Pat. Nos. 4,877,745; 5,449,754; 5,474,796; 5,658,802; 5,700,637; and 5,958,342; 6,221,653; and 6,242,266; as well as: 4,500,895; 4,771,295; 5,278,584; 5,305,015; 6,155,675; 6,155,676; 6,183,067; 6,290,331; the disclosures of which are herein incorporated by reference.

Of particular interest in many embodiments are fluid deposition devices where the subject printhead adjusters hold one or more multiple printhead die printheads, as described in U.S. patent application Ser. No. 10/023,375 titled "Pulse Jet Print Head Having Multiple Printhead Dies and Methods for Use in the Manufacture of Biopolymeric Arrays" filed on even date herewith); the disclosure of which is herein incorporated by reference. These printheads are characterized by having multiple printhead dies bonded to a surface of an orifice plate having multiple orifices to produce a printhead having at least one firing chamber, and typically a plurality of firing chambers.

Also of particular interest in many embodiments are fluid deposition devices where the subject printhead adjusters hold one or more multiple printhead die/multiple reservoir printhead assemblies, as described in U.S. patent application Ser. No. 10/022,088; the disclosure of which is herein incorporated by reference. These printheads are characterized by having a multiple printhead die printhead and a multiple reservoir housing affixed to the multiple die printhead.

The dies of the subject printheads and assemblies thereof may be piezoelectric or thermal pulse jet dies, (or another analogous pulse jet die) as is known in the art. The printheads and assemblies thereof found in the subject printhead adjusters are, in many embodiments, thermal pulse jet printheads. As is known to those of skill in the art, thermal pulse jet heads typically have at least the following components: (a) an orifice; (b) a firing chamber; and (c) a heating element. Thermal pulse jet heads and methods for their manufacture and use are described in a number of different U.S. patents, including: U.S. Pat. Nos. 5,772,829; 5,745, 128; 5,736,998; 5,736,995; 5,726,690; 5,714,989; 5,682, 188; 5,677,577; 5,642,142; 5,636,441; 5,635,968; 5,635, 966; 5,595,785; 5,477,255; 5,434,606; 5,426,458; 5,350, 616; 5,341,160; 5,300,958; 5,229,785; 5,187,500; 5,167, 776; 5,159,353; 5,122,812; and 4,791,435; the disclosures of which are herein incorporated by reference.

The subject non-contact fluid deposition devices that include the above described printhead adjusters are typically automated devices that are similar in construction to conventional inkjet or pulse-jet printing devices. Such automatic devices comprise at least a means for precisely controlling the position of the printhead adjuster/head component with respect to a substrate surface (an XYZ translational mechanism), e.g., an XYZ translational arm to which the adjuster is rigidly fixed, and for firing the head. Such automated devices are well known to those of skill in the printing and document production art, and are disclosed in U.S. Pat. Nos. 5,772,829; 5,745,128; 5,736,998; 5,736,995; 5,726,690; 5,714,989; 5,682,188; 5,677,577; 5,642,142; 5,636,441; 5,635,968; 5,635,966; 5,595,785; 5,477,255; 5,434,606; 5,426,458; 5,350,616; 5,341,160; 5,300,958; 5,229,785; 5,187,500; 5,167,776; 5,159,353; 5,122,812; and 4,791,435; the disclosures of which are herein incorporated by reference.

Methods of Using the Subject Multiple Reservoir/Multiple Die Printhead Assemblies In practicing the subject methods, a non-contact fluid deposition pulsejet device that includes the subject printhead adjuster, as described above, is loaded with a volume of the fluid to be deposited on the substrate surface. In certain preferred embodiments, the subject devices are employed to deposit fluids that include a biopolymer or a precursor thereof. In other words, the fluids of interest are ones that include a biopolymer or a biomonomer. Biopolymers are generally biomolecules (e.g., naturally occurring molecules found in living organisms or synthetic mimetics/analogues thereof, where biomolecules of interest include polypeptides, polysaccharides, nucleic acids and the like, as well as derivatives thereof, where of particular interest in many embodiments are nucleic acids, including oligonucleotides and polynucleotides, e.g., cDNA, or polypeptides, e.g., proteins or fragments thereof. Biopolymer precursors include activated monomers, e.g., activated amino acids and nucleotides, employed in step wise fabrication protocols in which biopolymeric ligands are grown on a surface of a substrate, as is known in the art. The fluid may or may not be aqueous, depending on the nature of the molecule to be delivered in the fluid. For example, biopolymeric molecules are typically delivered in an aqueous fluid, while activated monomers may require delivery in a non-aqueous fluid. The amount of fluid present in the at least one firing chamber may vary, but in many embodiments is at least about 10%, usually at least about 20% of the total volume of the firing chamber.

In practicing the subject methods, the printhead held in the adjuster is loaded with the fluid to be deposited. By loaded is meant that the fluid is at least introduced into a firing chamber of the device. The fluid may be loaded into the firing chamber and fluid reservoir (if present) using any convenient means. Thus, conventional methods of introducing ink into thermal inkjet heads may be employed. Where such methods are employed, following loading of the fluid sample into the pulse jet head, it is often desirable to "prime" the device prior to use. One means of priming the device is to apply sufficient pressure to the fluid in the reservoir (or conversely negative pressure to the orifice) such that a volume of fluid is forced out of the orifice. Such priming methods are currently employed in the printing industry and thus are well known to those of skill in the art.

Alternatively, where minimal waste of the fluid sample desired, e.g. where the fluid is an expensive or rare cDNA sample, the following "front loading" method of loading the fluid sample into the firing chamber and reservoir may be employed. In this method of fluid sample loading, the orifice is contacted with the fluid under conditions sufficient for fluid to flow through the orifice and into the firing chamber of the head, where fluid flow is due, at least in part, to capillary forces. To assist in the flow of fluid into the orifice, back pressure in the form of suction (i.e. negative pressure) may be applied to the firing chamber (and reservoir, if present) of the head, where the back pressure will typically be at least about 5, and may be at least about 10 and even as great as about 100 inches of $H_2O$ or more. In general, each firing chamber (and reservoir with which it is in fluid communication, if present) is subjected to the same back pressure. For a further description of this front loading procedure, see e.g., U.S. Pat. No. 6,323,043 the disclosure of which is herein incorporated by reference.

The amount of fluid required to load the head is typically small, generally not exceeding more than about 10 $\mu$l, usually not exceeding more than about 5 $\mu$l and in many embodiments not exceeding more than about 2 $\mu$l. As such, the amount of fluid that is wasted in readying or preparing the thermal pulsejet head for firing is minimal. As such, fluid loading is highly efficient. Therefore, the subject methods are particularly suited for use with rare and/or expensive fluid samples.

Figure 6:
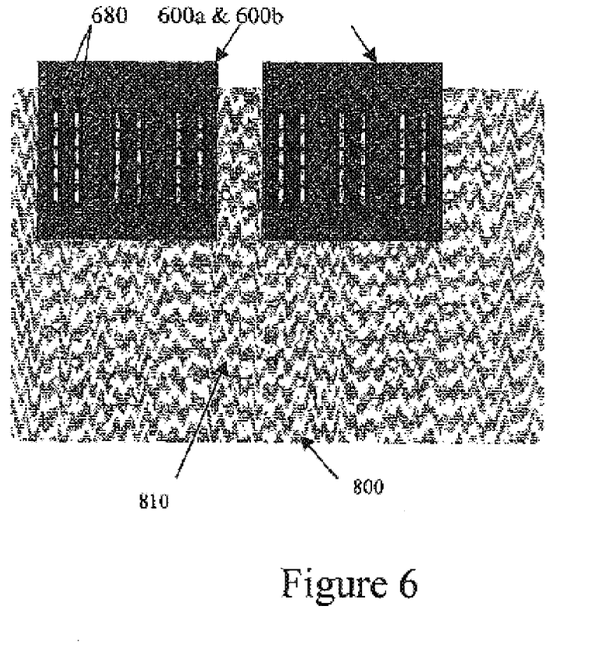
FIG. 6 provides a representation of how the device shown in FIGS. 3 and 4 can be rapidly loaded from a standard 384 well microtitre plate.

In those embodiments where the printhead adjuster includes multiple, e.g., two, different housings each holding a multiple printhead die/multiple reservoir printhead assembly in side by side configuration, e.g., as shown in FIGS. 3 and 4, fluid can be loaded rapidly and efficiently into the firing chambers and reservoirs of the printhead assemblies from standard multiwell plates, e.g., 384 well microtitre plates. FIG. 6 provides a representation of how the device shown in FIGS. 3 and 4 can be rapidly loaded from a standard 384 well microtitre plate. FIG. 6 shows microtitre plate 800 with 384 different wells 810. Positioned over the top of the plate 800 are printheads 600a and 600b held by the printhead adjuster. Reservoirs 680 of the printheads are clearly visible. The reservoirs are lined up with the wells so that sixty samples are rapidly picked up, by picking up an initial 20 samples, stepping the heads to the right, picking up an additional 20 samples, stepping the heads to the right, and then picking up the last 20 samples. As such, the procedure depicted in FIG. 6 is a sequential front loading procedure, in which the row or sets of rows of a multiple die, multiple reservoir printhead are sequentially front loaded (see e.g., U.S. application Ser. No. 09/150,507; the disclosure of which is herein incorporated by reference) with fluid from a multiple fluid container element, e.g., microtitre plate. Thus, where one has a multiple die, multiple reservoir printhead assembly in which there are at least two spaced apart dies and each die is in contact with at least one row of reservoirs, the printhead assembly is loaded by aligning a first row of reservoirs with a first row of wells and frontloading the reservoirs, followed by an alignment, e.g., by stepping or moving the printhead assembly in the appropriate direction, of a second row of reservoirs with a second row of wells and frontloading the reservoirs. For example, in FIG. 6, the multiple die, multiple reservoir printhead assembly has three spaced apart dies, where each die contacts a set of two rows of reservoirs. To load the reservoirs, a right most set of reservoirs is first aligned with a first set of two rows of wells of the microtitre plate and front loaded. The printhead assembly is then stepped to the right and the middle row of reservoirs is aligned with a second row of wells and front loaded. Finally, the printhead assembly is stepped to the right one more time and the left set of reservoirs is aligned with a third row of wells and front loaded. While the above description has been made in terms of loading each row of reservoirs with fluid from a different row of wells, the process may be modified so that the two or more rows of reservoirs are loaded from the same row of wells.

Following loading of the printer head, e.g., by front loading as described above, the head is employed to deposit a quantity of at least one fluid sample, and generally a plurality of distinct fluid samples—one from each distinct firing chamber, onto the surface of a substrate. As the subject methods are capable of depositing an extremely small volume of fluid onto a substrate surface, the subject methods can be used to deposit a pico liter quantity of fluid onto a substrate, e.g., an array, surface. By "pico liter quantity" is meant a volume of fluid that is at least about 0.1 $\mu$l, usually at least about 1 $\mu$l and more usually at least about 10 $\mu$l, where the volume may be as high as 250 $\mu$l or higher, but generally does not exceed about 100 nL and usually does not exceed about 1 $\mu$l.

A feature of the subject methods is that the deposition process does not result in a substantial modulation of the activity or functionality of the biopolymers/biomonomers of interest in the fluid that is deposited, despite the small volumes front loaded into the head and the thermal pulsejet deposition protocol employed. In other words, the overall activity/functionality of interest in the fluid that is deposited from the pulsejet during the subject methods is not substantially different from the overall activity in the fluid loaded into the pulsejet prior to deposition.

In the broadest sense, the subject methods may be used to deposit a volume of fluid sample onto any structure, specifically a surface, of any substrate, where the substrate may be a planar structure, e.g., a slide, a reagent container, e.g., a well in a multi-well plate (such as the bottom of a well), a channel or micro structure, an array etc.

To deposit fluid onto the substrate surface according to the subject methods, the loaded pulse jet head is positioned in opposing relationship relative to the surface of the substrate (e.g. with an XYZ translational means), where the orifice is in opposition to the position on the array surface at which deposition of the protein solution is desired (e.g. opposite a binding agent spot on the array). The distance between the orifice and the substrate surface will not be so great that the volume of protein fluid cannot reach the substrate surface and produce a spot in a reproducible manner. As such, the distance between the orifice and the substrate surface will generally range from about 10 m to 10 mm, usually from about 100 m to 2 mm and more usually from about 200 m to 1 mm.

After the head is placed into position relative to the substrate surface, the pulse jet head is actuated to dispense a volume of fluid. For thermal pulse jet heads, the temperature of the heating elements or resistors of the head is raised to a temperature sufficient to vaporize a portion of the fluid immediately adjacent to the resistor and produce a bubble. In raising the temperature of the heating element, the temperature of the heating element is raised to at least about 100° C., usually at least about 400° C. and more usually at least about 700° C., where the temperature may be raised as high as 1000° C. or higher, but will usually be raised to a temperature that does not exceed about 2000° C. and more usually does not exceed about 1500° C. As such, a sufficient amount of energy will be delivered to the resistor to produce the requisite temperature rise, where the amount of energy will generally range from about 1.0 to 100 J, usually from about 1.5 to 15 J. The portion of fluid in the firing chamber that is vaporized will be sufficient to produce a bubble in the firing chamber of sufficient volume to force an amount of liquid out of the orifice.

The formation of the bubble in the firing chamber traps a portion or volume of the fluid present in the firing chamber between the heating element and the orifice and forces an amount or volume of fluid out of the orifice at high speed. The amount or volume of fluid that is forced out of the firing chamber can be controlled depending on the specific amount of fluid that is desired to be deposited on the substrate. As is known in the art, the amount of fluid that is expelled can be controlled by changing one or more of a number of different parameters of the pulse jet head, including: the orifice diameter, the orifice length (depth), the size of the firing chamber, the size of the heating element, and the like. Such variations are well known to those of skill in the art. As such, the amount or volume of fluid that is forced out or expelled from the firing chamber may range from about 0.1 to 2000 μl, usually from about 0.5 to 500 μl and more usually from about 1.0 to 250 μl. The speed at which the fluid is expelled from the firing chamber is at least about 1 m/s, usually at least about 10 m/s and may be as great as about 20 m/s or greater.

Upon actuation of the thermal pulse jet head of the subject invention, as described above, fluid is expelled from the orifice and travels to the substrate surface. Upon contact with the substrate surface, the deposited fluid typically forms a spot on the substrate surface. As mentioned above, by varying the design parameters of the thermal pulsejet head, the spot dimensions can be controlled such that spots of various sizes can be produced. With the subject methods, one can produce spot sizes that have diameters ranging from a minimum of about 10 m to a maximum of about 1.0 cm. In those embodiments where very small spot sizes are desired, one can produce small spots that have a diameter ranging from about 1.0 m to 1.0 mm, usually from about 5.0 m to 500 m and more usually from about 10 m to 200 m. In many embodiments, the spot sizes range from about 30 to 100 m in diameter.

In certain embodiments, it may be desirable to prevent evaporation of the fluid sample following deposition. Evaporation may be prevented in a number of different ways. The subject methods may be carried out in a high humidity environment. By "high humidity" is meant an environment in which the humidity is at least about 86% relative humidity, usually at least about 95% relative humidity and more usually at least about 99% relative humidity. Alternatively, one may apply an evaporation retarding agent, e.g. mineral oil, glycerol solution, polyethylene glycol, etc., over the surface of the deposited sample, e.g. by using a thermal pulsejet as described above.

Where desired, following deposition of the desired amount of protein fluid, the individual firing chambers of the heads may be washed and front loaded with another fluid for subsequent fluid deposition. Washing of the head can be accomplished using any convenient protocol, e.g., via front loading and expelling an appropriate wash buffer, one or more times, by backloading and expelling an appropriate wash buffer, etc. In addition, the head may be manually or automatically wiped clean to remove any sample/wash solution left from the previous deposition.

In many embodiments, the head is rapidly washed and reloaded with a new solution, such that the time period starting from the deposition of the first fluid to the loading of the second fluid, i.e., the washing time, is extremely short.

In these embodiments, the wash time typically does not exceed about 1 minute, usually does not exceed about 5 minutes and more usually does not exceed about 30 minutes. The wash protocol in these embodiments may include a single flushing or multiple flushes, where the total number of flushes will typically not exceed about 3, usually will not exceed about 5 and more usually will not exceed about 10. The wash fluid employed in these embodiments is typically one that provides for removal of substantially all bipolymers/biomonomers of the first fluid in a minimal number of flushes, where representative fluids of interest include, but are not limited to: saline buffer solution with surfactant, and the like.

The above methods can be substantially, if not completely automated, so that fluid can be loaded and deposited onto a surface automatically. As such, the subject methods are amenable to high throughput applications, e.g., high throughput manufacturing applications. In automated versions of the subject methods, automated devices are employed that are similar in construction to conventional thermal inkjet printing devices, with the exception that the thermal pulsejet head of the device is front loaded with a fluid sample as described above. Such automatic devices comprise at least a means for precisely controlling the position of the head with respect to an array surface (an XYZ translational mechanism) and for firing the head. Such automated devices are well known to those of skill in the art and are disclosed in U.S. Pat. Nos. 6,242,266; 6,232,072; and 6,180,351; the disclosures of which are herein incorporated by reference.

A feature of the subject invention is that before fluid loading and/or deposition as described above, the one or more printheads held in the frame are adjusted using the printhead housing's set of individual axis adjustment elements. For example in the representative printhead adjuster shown in FIG. 4, the printhead housing is adjusted in the X direction by turning the two side screws 910*a* and 910*b* by the same amount. The printhead housing is adjusted in the Y direction by turning the one front screw 920 by an appropriate amount. The printhead housing is adjusted in the Z direction by turning the three top screws 930*a*, 930*b* and 930*c* by the same amount. The printhead housing is adjusted in the theta about X direction by turning the rear top screw 930*c* in one direction and the front two top screws 930*a* and 930*b* in the opposite direction by the same amount. The printhead housing is adjusted in the theta about Y direction by turning the inner top screw 930*a* in one direction and the outer two screws 930*b* and 930*c* in the opposite direction by the same amount. The printhead housing is adjusted in the theta about Z direction by turning the one side screw, e.g., 920 in one direction, and the other side screw(s), e.g., 910*a* and 910*b*, in the opposite direction by the same amount.

In many embodiments, the system provides the operator, via touch probes and cameras (elements well known to those of skill in the art) instructions with respect to how much and which direction to turn each screw, to bring the one or more printheads in the frame into proper adjustment or position, e.g. for loading and/or depositing fluid. With appropriate feedback from the system and slight movements of the adjustment elements, the adjuster can adjust each axis of adjustment within a tolerance of a few microns, where by few microns is meant less than about 10 microns, and often less than about 5 microns, which feature arises from the fine pitch screw component of those embodiments which include fine pitch screw adjustment elements. The subject adjuster can adjust the orifice location of the printheads held in the adjuster to within 10 to 20 microns in all horizontal axes (e.g., X, Y and theta about Z) and to within 10 to 40 microns in all vertical axes (e.g., Z, theta about X and theta about Y).

Features of the subject adjusters provide for efficient and accurate initial placement and/or replacement of printhead assemblies in the housings of the adjusters. As mentioned above, the printhead housing includes alignment means which provide for alignment of the printhead assembly in the housing. Because of the alignment means, the printheads are repeatedly placed in the housing with little variation in orifice positioning of the printhead. In addition, the housing includes elements (e.g., the compression elements), described above, that provide for quick and reliable electrical and fluid connection upon placement or replacement of a printhead assembly in the housing.

The subject methods of depositing a volume of fluid sample onto the surface of a substrate find use in a variety of different applications, and are particularly suited for use in methods where reproducible placement of small volumes of a reagent onto the surface of a solid support are desired. As such, the subject methods find use in the preparation and manufacture of biosensors, microarrays, e.g., genomic and proteomic arrays, microfluidic devices, and the like.

In the course of practicing the subject methods, fluid contacted arrays are produced in which each deposited fluid volume occupies a small area, i.e. spot, on the substrate surface. By small is meant that each fluid sample spot on the array has a diameter that is at least about 1 $\mu$m, usually at least about 5 $\mu$m and more usually at least about 10 $\mu$m and does not exceed about 10 mm, usually does not exceed about 1000 $\mu$m and more usually does not exceed about 200 $\mu$m.

Because of the subject printheads employed, a plurality of distinct or different fluids can be simultaneously deposited on a substrate surface with great precision, accuracy and reproducibility. As a plurality of distinct fluids can be simultaneously deposited, the number of different fluids simultaneously deposited is typically at least 2, where the number may be at least about 5, at least about 10, at least about 15 or more, where the upper limit may vary greatly, including about 50, about 100, about 200 or higher. By great precision is meant that the fluids can be precisely printed onto a substrate surface so as to produce a high density array of spots, where by high density is meant at least about 1000, usually at least about 2,500 and sometimes at least about 10,000 sposts/cm². As the subject methods are reproducible, any variation from array to array produced using a given printhead, as measured by variation of diameter of a given spot, does not exceed about 0.5 fold, and usually does not exceed about 0.25 fold.

A variety of different arrays can be produced according to the subject methods.

Arrays

Also provided by the subject invention are novel arrays of polymeric binding agents produced using the subject printheads, as described above. The subject arrays include at least two distinct polymers that differ by monomeric sequence immobilized on e.g., covalently or non-covalently attached to, different and known locations on the substrate surface. Each distinct polymeric sequence of the array is typically present as a composition of multiple copies of the polymer on the substrate surface, e.g. as a spot on the surface of the substrate. The number of distinct polymeric sequences, and hence spots or similar structures, present on the array may vary, but is generally at least 2, usually at least 5 and more usually at least 10, where the number of different spots on the array may be as a high as 50, 100, 500, 1000, 10,000 or higher, depending on the intended use of the array. The spots of distinct polymers present on the array surface are generally present as a pattern, where the pattern may be in the form of organized rows and columns of spots, e.g. a grid of spots, across the substrate surface, a series of curvilinear rows across the substrate surface, e.g. a series of concentric circles or semi-circles of spots, and the like. The density of spots present on the array surface may vary, but will generally be at least about 10 and usually at least about 100 spots/cm², where the density may be as high as $10^6$ or higher, but will generally not exceed about $10^5$ spots/cm².

In the broadest sense, the arrays of the subject invention are arrays of polymeric binding agents, where the polymeric binding agents may be any of: peptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini, e.g. the 3' or 5' terminus. In other embodiments, the arrays are arrays of polypeptides, e.g., proteins or fragments thereof.

Utility

The subject arrays find use in a variety applications, where such applications are generally analyte detection applications in which the presence of a particular analyte in a given sample is detected at least qualitatively, if not quantitatively. Protocols for carrying out such assays are well known to those of skill in the art and need not be described in great detail here. Generally, the sample suspected of comprising the analyte of interest is contacted with an array produced according to the subject methods under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g. through use of a signal production system, e.g. an isotopic or fluorescent label present on the analyte, etc. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g. a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

Where the arrays are arrays of polypeptide binding agents, e.g., protein arrays, specific applications of interest include analyte detection/proteomics applications, including those described in: U.S. Pat. Nos. 4,591,570; 5,171,695; 5,436,170; 5,486,452; 5,532,128; and 6,197,599; the disclosures of which are herein incorporated by reference; as well as published PCT application Nos. WO 99/39210; WO 00/04832; WO 00/04389; WO 00/04390; WO 00/54046; WO 00/63701; WO 01/14425; and WO 01/40803; the disclosures of the United States priority documents of which are herein incorporated by reference.

In certain embodiments, the subject methods include a step of transmitting data from at least one of the detecting and deriving steps, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

As such, in using an array made by the method of the present invention, the array will typically be exposed to a sample (for example, a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array. For example, a scanner may be used for this purpose which is similar to the AGILENT MICROARRAY SCANNER scanner available from Agilent Technologies, Palo Alto, Calif. Other suitable apparatus and methods are described in U.S. patent applications Ser. No. 09/846125 "Reading Multi-Featured Arrays" by Dorsel et al.; and Ser. No. 09/430214 "Interrogating Multi-Featured Arrays" by Dorsel et al. As previously mentioned, these references are incorporated herein by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing).

It is evident from the above results and discussion that subject invention provides for many improvements non-contact fluid deposition. The printhead adjuster component of the subject invention provides for highly accurate adjustment of a printhead assembly held therein in multiple different axes, providing for extremely specific control of the fluid deposition process.

The subject invention provides numerous specific benefits in the field of biopolymer microarray production. For example, in those embodiments where an adjuster includes two side-by-side printheads, the adjuster allows adjustment of the printheads in such a way that the printheads can draw fluid samples from standard microtitre or analogous multi-well plates and proceed to print high quality microarrays. The printheads can be aligned very precisely and reliably, and the position is not lost during writing or washing because of the rigid design of the adjuster and the reliability of the spring/adjust system that holds the heads in the frame of the adjuster. Furthermore, down time of the system is minimized because of the design of the adjuster and its interface with the printhead assembly, which requires only minimal adjustment upon replacement of the printhead. The design of the housing in the printhead adjuster minimizes the complexity and time to replace the heads, while retaining a high degree of reliability. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A non-contact fluid deposition device, said device comprising:
   (a) a non-contact fluid deposition printhead adjuster comprising:
      (i) a single rigid frame;
      (ii) at least one printhead housing; and
      (iii) a set of axis adjustment elements comprising at least one horizontal adjustment element and a vertical adjustment element, where said set further includes a rotational axis adjustment element for each horizontal and vertical axis adjustment element of said set; and
   (b) a movement arm rigidly attached to said frame of said adjuster for moving said adjuster, and any printheads operationally attached thereto, relative to a printing substrate.

2. The device according to claim 1, wherein said set of axis adjustment elements comprises six multiple axis adjustment elements which include two horizontal axis adjustment elements, one vertical axis adjustment element and a rotational axis adjustment element for each of said horizontal and vertical axis adjustment elements.

3. The device according to claim 2, wherein said six axis adjustment elements are: X axis adjustment element; theta about X axis adjustment element; Y axis adjustment element; theta about Y axis adjustment element; Z axis adjustment element; and theta about Z axis adjustment element.

4. The device according to claim 1, wherein each axis adjustment element comprises a fine pitch screw.

5. The device according to claim 1, wherein said printhead housing is held in said frame by at least one substantially frictionless screw/spring holding element that holds said housing relative to said frame in a manner that allows movement of said housing without sliding friction from said spring component of said holding element.

6. The device according to claim 5, wherein said screw of said holding element has an outer diameter that is smaller than the inner diameter of said spring.

7. The device according to claim 1, wherein said adjuster comprises multiple printhead housings each having its own set of axis adjustment elements.

8. The device according to claim 7, wherein said adjuster comprises two printhead housings.

9. The device according to claim 1, wherein each printhead housing of said adjuster comprises an alignment element for precisely aligning a printhead placed therein.

10. The device according to claim 1, wherein said device comprises a detector to capture an image of the drops after use of the device in fluid deposition.

11. The device according to claim 1, wherein said housing comprises a compression element for establishing a fluid seal between an external fluid line and a printhead in said housing.

12. The device according to claim 11, wherein said compression element comprises an engaging screw.

13. The device according to claim 1, wherein said housing comprises a compression element for establishing electrical connection between a printhead in said housing and an electrical connector board in said housing.

14. The device according to claim 13, wherein said compression means is a thumb screw.

15. The device according to claim 1, wherein a printhead is present in said at least one printhead housing.

16. The device according to claim 15, wherein said printhead is a pulse jet printhead.

17. The device according to claim 16, wherein said printhead is part of a multiple die, multiple reservoir printhead assembly.

18. The device according to claim 17, wherein said printhead comprises at least one firing chamber containing a volume of a fluid that includes a biopolymer or precursor thereof.

19. A non-contact fluid deposition device, said device comprising:
(a) a non-contact fluid deposition printhead adjuster comprising:
  (i) a single rigid frame;
  (ii) two individual printhead housings held in side-by-side configuration in said single rigid frame; and
  (iii) a set of axis adjustment elements comprising at least one horizontal adjustment element and a vertical adjustment element, where said set further includes a rotational axis adjustment element for each horizontal and vertical axis adjustment element of said set; and
(b) a movement arm rigidly attached to said frame of said adjuster for moving said adjuster, and any printheads operationally attached thereto, relative to a printing substrate.

20. The device according to claim 19, wherein each of said housings is held in said single rigid frame by six axis adjustment elements which include two horizontal axis adjustment elements, one vertical axis adjustment element an a rotational axis adjustment element for each of said horizontal and vertical axis adjustment elements.

21. The device according to claim 20, wherein said six axis adjustment elements are: X axis adjustment element; theta about X axis adjustment element; Y axis adjustment element; theta about Y axis adjustment element; Z axis adjustment element; and theta about Z axis adjustment element.

22. The device according to claim 19, wherein each axis adjustment element comprises a fine pitch screw.

23. The device according to claim 22, wherein each of said printhead housings is held in said frame by at least one substantially frictionless screw/spring holding element that holds said housing relative to said frame in a manner that allows movement of said housing without sliding friction from said spring component of said holding element.

24. The device according to claim 23, wherein said screw of said holding element has an outer diameter that is smaller than the inner diameter of said spring.

25. The device according to claim 19, wherein each printhead housing of said adjuster comprises an alignment element for precisely aligning a printhead placed therein.

26. The device according to claim 25, wherein said aligning element comprises at least two dowel pins.

27. The device according to claim 19, wherein said housings each comprise a compression element for establishing a fluid seal between an external fluid line and a printhead in said housing.

28. The device according to claim 27, wherein said compression element comprises an engaging screw.

29. The device according to claim 19, wherein said housings each comprise a compression element for establishing electrical connection between a printhead in said housing and an electrical connector board in said housing.

30. The device according to claim 29, wherein said compression means is a thumb screw.

31. The device according to claim 19, wherein a printhead is present in each of said printhead housings.

32. The device according to claim 31, wherein said printhead is a thermal pulse jet printhead.

33. The device according to claim 32, wherein said printhead is part of a multiple die, multiple reservoir printhead assembly.

34. The device according to claim 33, wherein said printhead comprises at least one firing chamber containing a volume of a fluid that includes a biopolymer or precursor thereof.

35. A method of depositing a volume of a fluid on a surface of a substrate, said method comprising:
(a) positioning a printhead comprising adjuster of a device according to claim 1 in opposing relation to said substrate surface; and
(b) actuating said printhead to expel a volume of said fluid onto said substrate surface.

36. The method according to claim 35, wherein said fluid contains a biopolymer or precursor thereof.

37. The method according to claim 36, wherein said method further comprises depositing a volume of a second fluid containing a biopolymer or precursor thereof onto said substrate surface.

38. The method according to claim 35, wherein said method is a method of making a biopolymer array.

39. The method according to claim 38, wherein said biopolymer is selected from the group consisting of polypeptides and nucleic acids.

40. The method according to claim 37, wherein said precursor is selected from the group consisting of amino acids and nucleotides.

41. An automated non-contact printing system, said system comprising a printhead loaded device according to claim 15, wherein said printhead loaded device comprises a fluid.

42. The system according to claim 41, wherein said fluid comprises a biopolymer or a precursor thereof.

43. A non-contact fluid deposition printhead adjuster comprising:
(a) a single rigid frame;
(b) at least one printhead housing; and
(c) and a set of axis adjustment elements comprising a rotational axis adjustment element for each horizontal and/or vertical axis adjustment element of said set.

44. The adjuster according to claim 43, wherein said set of axis adjustment elements comprises six axis adjustment elements.

45. The adjuster according to claim 44, wherein said six axis adjustment elements are: X axis adjustment element; theta about X axis adjustment element; Y axis adjustment element; theta about Y axis adjustment element; Z axis adjustment element; and theta about Z axis adjustment element.

46. The adjuster according to claim 43, wherein each axis adjustment element comprises a fine pitch screw.

47. The adjuster according to claim 43, wherein said printhead housing is held in said frame by at least one substantially frictionless screw/spring holding element that holds said housing relative to said frame in a manner that allows movement of said housing without sliding friction from said spring component of said holding element.

48. The adjuster according to claim 47, wherein said screw has an outer diameter that is smaller than the inner diameter of said spring.

49. The adjuster according to claim 43, wherein said adjuster comprises multiple printhead housings each having its own set of axis adjustment elements.

50. The adjuster according to claim 49, wherein said adjuster comprises two printhead housings.

51. The adjuster according to claim 43, wherein each printhead housing of said adjuster comprises an alignment element for precisely aligning a printhead placed therein.

52. The adjuster according to claim 51, wherein said aligning element comprises at least two dowel pins.

53. The adjuster according to claim 43, wherein said housing comprises a compression element for establishing a fluid seal between an external fluid line and a printhead in said housing.

54. The adjuster according to claim 53, wherein said compression element comprises an engaging screw.

55. The adjuster according to claim 43, wherein said housing comprises a compression element for establishing electrical connection between a printhead in said housing and an electrical connector board in said housing.

56. The adjuster according to claim 55, wherein said compression means is a thumb screw.

57. The method according to claim 35, wherein said set of axis adjustment elements of said printhead comprising adjuster comprises six multiple axis adjustment elements which include two horizontal axis adjustment elements, one vertical axis adjustment element and a rotational axis adjustment element for each of said horizontal and vertical axis adjustment elements.

58. The method according to claim 57, wherein said axis adjustment elements are: X axis adjustment element; theta about X axis adjustment element; Y axis adjustment element; theta about Y axis adjustment element; Z axis adjustment element; and theta about Z axis adjustment element.

59. The method according to claim 35, wherein each axis adjustment element of said printhead comprising adjuster comprises a fine pitch screw.

60. The method according to claim 35, wherein said printhead housing of said printhead comprising adjuster is held in said frame by at least one substantially frictionless screw/spring holding element that holds said housing relative to said frame in a manner that allows movement of said housing without sliding friction from said spring component of said holding element.

61. The method according to claim 60, wherein said screw of said holding clement has an outer diameter that is smaller than the inner diameter of said spring.

62. The method according to claim 59, wherein said adjuster comprises multiple printhead housings each having its own set of axis adjustment elements.

* * * * *